(12) United States Patent
Rogler et al.

(10) Patent No.: US 6,864,402 B1
(45) Date of Patent: Mar. 8, 2005

(54) CHRONIC HEPATITIS VIRUS INFECTION AND CLONAL HEPATOCELLULAR CARCINOMA IN MOUSE REPOPULATED LIVERS

(75) Inventors: Charles E. Rogler, Lawthorne, NY (US); Joerg Petersen, Hamburg (DE)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/344,189

(22) Filed: Jun. 24, 1999

Related U.S. Application Data

(63) Continuation-in-part of application No. 09/156,892, filed on Sep. 18, 1998, now abandoned.

(51) Int. Cl.$^7$ ..................... G01N 33/00; A01K 67/027; C12N 15/00
(52) U.S. Cl. ................. 800/3; 800/18; 800/25
(58) Field of Search .............................. 800/3, 18, 25, 800/9, 10, 22

(56) References Cited

U.S. PATENT DOCUMENTS 5,583,278 A * 12/1996 Alt et al. ........................ 800/2
5,980,886 A * 11/1999 Kay et al. ................. 424/93.21
6,034,297 A * 3/2000 Vierling ......................... 800/9

FOREIGN PATENT DOCUMENTS

EP   WO 94/02601   2/1994 ........... C12N/15/00

OTHER PUBLICATIONS

M Houghton, Fields Virology, 3rd. Ed., "Hepatitis C Viruses," Chap.32, pp. 1035–1036.*
WS Robinson, Fundamental Virology, 2nd Ed., "Hepadnaviridae and Their Replication," 1991 Chap. 38, pp. 989–1021.*
FB Hollinger et al., Fields Virology, "Hepatitis A Virus," 3rd. Ed., Chap.24, pp. 735 and 751–752.*
RH Purcell, Fields Virology, "Hepatitis E Virus," 3rd. Ed., Chap. 89, pp. 2831–2836.*
GL Burngardner et al., Immunological Reviews, " Unusual patterns of alloimmunity evoked by allogeneic liver parenchymal cells," 2000, vol. 174, pp. 260–279.*
Kuby et al, 1994, Immunology, 2nd edition, Freeman Press, p. 26.*
Chisari, F.V. et al. (1995) *Annu. Rev. Immunol.* 13:29–60.
Chisari, F.V. (1996) *Curr Topics Microbiol Immunol* 206:150–173.
Guidotti, L.G. et al. (1994) *Proc. Natl. Acad. Sci. USA* 91:3764–3768.
Guidotti, L. G. et al. (1996) *Immunity* 4:25–36.
Gupta, S. et al. (1996) *Prog Liv Dis* 14:199–222.
Sandgren, E.P. et al. (1991) *Cell* 66:245–256.
Rhim, J.A. et al. (1994) *Science* 263:1149–1152.
Rhim, J.A., et al. (1995) *Proc. Natl. Acad. Sci. USA* 92:4942–4946.
Roggendorf, M. et al. (1995) Intervirology 38:100–112.
Korba, B.E. et al. (1989) *J. Virol* 63:1360–70.
Tennant, B.C. et al. (1994) in *The Liver. Biologyand Pathobiology*, eds. Arias, I.M., et al. (Raven Press,. New York) pp 1455–1469.
Shinkai, Y. et al. (1992) *Cell* 68:855–867.
Overturf, K. et al. (1996) *Nature Genetics* 12:266–273.
Grompe, M. et al. (1993) *Genes and Development* 7:2298–2307.
Overturf, K. et al. (1997) *Am. J. Path.* 151:1273–1280.
Marie–Jeanne, T. et al. (1997) *Hepatology* 25:884–888.
Petersen, J. et al. (Sep. 1997) Abstract No. 041, Molecular Biology of Hepatitis B Viruses, Institut Pasteur.
Petersen, J. et al. (1998) *Proc. Natl. Acad. Sci. USA* 95:310–315.
Petersen, J. et al. (1997) *Hepatology* 26(4), pt. 2, 225A, Abstract # 387.
Kedda, Mary–Anne, et al., "Susceptibility of Chacma Baboons (Papio Ursinus Orientails) To Infection By Hepatitis B Virus", *Transplantation*, 69:1429–1434 (2000).
Michaels, Marian G, et al., "Lack of Susceptibility of Baboons To Infection With Hepatitis B Virus " *Transplantation*, 61:350–351 (1996).

* cited by examiner

*Primary Examiner*—Peter Paras, Jr.
(74) *Attorney, Agent, or Firm*—Darby & Darby

(57) ABSTRACT

A method is provided for repopulating degenerated of immunetolerant mice which lack mature B and T lymphocytes with xenogenic mammalian hepatocytes, particularly primate hepatocytes to generate chimeric mice. In addition, a method of generating a human hepatitis virus-infected chimeric mouse is provided. A preferred xenogenic primate hepatocyte is derived from human, chimpanzee or baboon. These chimeric mice are useful in the investigation of host and viral mechanisms determining hepadnaviral persistence and hepatocarcinogenesis. Methods for monitoring the development of hepatitis and hepatocellular carcinoma as well as methods for testing and screening anti-viral and anti-cancer compounds with this model system are also provided.

46 Claims, 8 Drawing Sheets

(3 of 8 Drawing Sheet(s) Filed in Color)

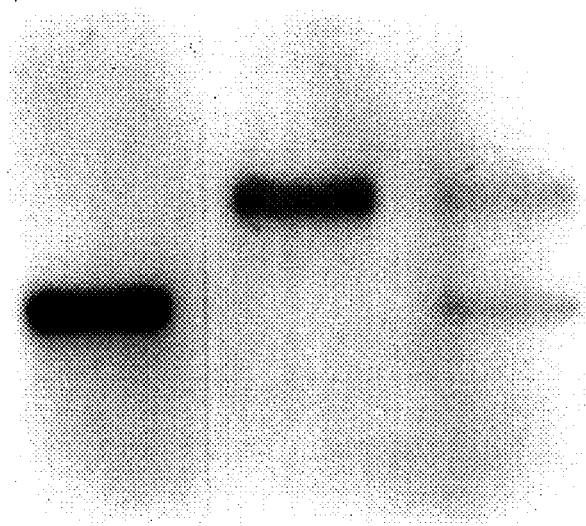
FIG. 1
FIG. 2A
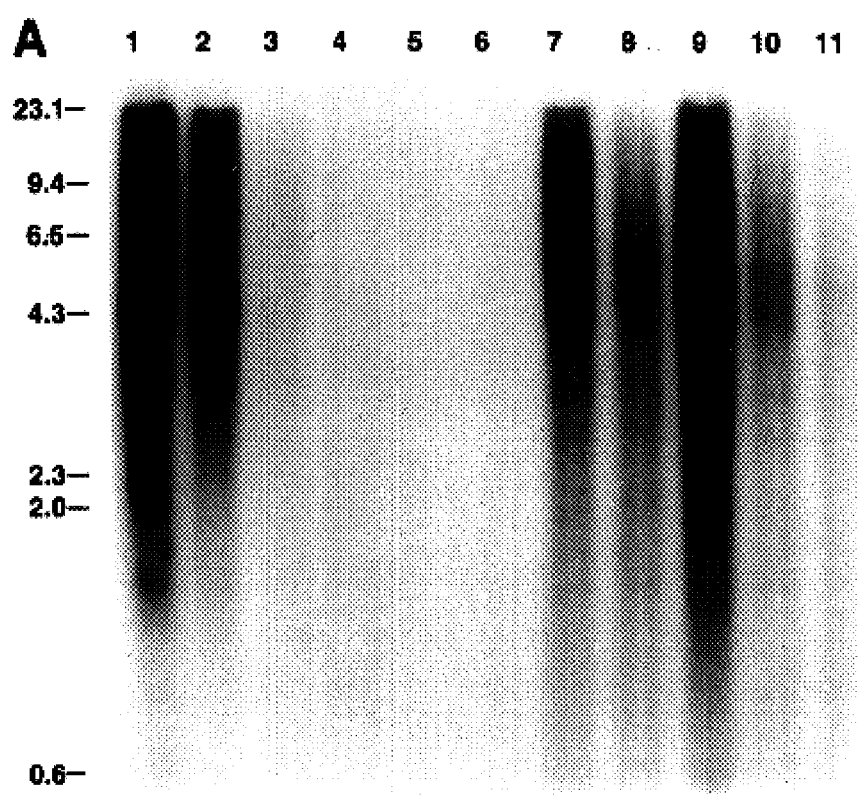

FIG. 4

CHRONIC HEPATITIS VIRUS INFECTION AND CLONAL HEPATOCELLULAR CARCINOMA IN MOUSE REPOPULATED LIVERS

This is a continuation-in-part of application Ser. No. 09/156,892, filed Sep. 18, 1998 abandoned which is hereby incorporated herein by reference, in its entirety.

This invention was made with Government support under U.S. Public Health Service Grant Nos. CA 37232 and DK 46952. The Government has certain rights in the invention.

FIELD OF THE INVENTION

The present invention pertains to chimeric mice repopulated with xenogenic mammalian hepatocyte's which can be infected with at least one compatible mammalian hepatitis virus. The invention also pertains to methods of making such mice and to methods of using the chimeric mice in the study of viral replication, hepatocellular carcinoma and treatment of these conditions.

BACKGROUND OF THE INVENTION

[Within this application several publications are referenced by Arabic numerals within parentheses. Full citations for these references, listed in sequence, may be found at the end of the specification. All of the cited references are incorporated by reference in their entirety.]

Hepatitis B virus (HBV) infection remains a major health problem with more than 350 million chronic HBV carriers worldwide who are at risk for developing liver cirrhosis and hepatocellular carcinoma (HCC) (1, 2, 3, 4). The development of effective therapies for eradicating HBV in chronic carriers has been limited by an incomplete understanding of the mechanisms of viral persistence (5).

HBV is a member of the hepadnavirus family of mammalian hepatitis viruses. HBV is a human virus which can also infect other primates, such as chimpanzee, as well as human hepatocellular carcinoma cells, such as HepG2 and Huh7. Other hepadnaviruses include Woodchuck Hepatitis Virus (WHV) which is native to the woodchuck *Marmotta monax* and can also infect the ground squirrel, as well as the Ground Squirrel Hepatitis Virus (GSHV) which infects the ground squirrel. Avian hepadnaviruses have been isolated from the duck (DHBV) and the heron (HHBV). In addition to the hepadnaviruses, there are other hepatitis viruses including, for example, Hepatitis A, C, E and F viruses, as well as Hepatitis Delta which requires the presence of Hepatitis B as a helper virus.

Interferon-alpha is the only currently approved treatment for persistent HBV infection (5, 6, 7). Besides exhibiting various immunomodulatory effects (B), interferon-alpha induces the release of intracellular enzymes such as 2'5'-oligoadenylate synthetase and double-stranded RNA-dependent protein kinase, which degrade viral messenger RNAs and inhibit viral protein synthesis (8) in vitro (9) and in vivo (6, 10). Patients who respond to interferon-alpha therapy show a decrease in circulating HBV DNA levels within the first week (8).

Both humoral and cellular elements of the host immune response are important for HBV clearance. The humoral response to HBV antigens, i.e. antibodies to hepatitis B surface antigen (anti-HBs), helps clear circulating virions and confers protection against reinfection, whereas T cell-mediated responses eliminate infected host cells (11, 12). HBV transgenic mice have been developed which replicate wild type HBV under the control of a full length HBV transgene inserted into the mouse genome. Recent work using these HBV transgenic mice has shown that this replication process can be altered by murine cytokines, such as tumor necrosis factor alpha and interferon gamma. These cytokines have the capacity to downregulate HBV replication in a noncytopathic manner (13, 14). It is therefore of interest to determine whether hepatitis virus replication will become persistent in the absence of B and T cells in the host, and whether acute infection of hepatocytes, in such an environment, would lead to viral persistence in all or some cases.

HBV transgenic mice have provided important new information regarding viral pathobiology (11, 12, 13, 14). However, HBV replication in these mice does not occur by an identical mechanism to that which occurs in naturally infected hepatocytes. In the transgenic HBV mice, replication is driven by an integrated transgene in the mouse chromosome. As a result, the hepatocytes can never be completely "cured" of their HBV genomes. In contrast, in hepatocytes which are natural hosts for hepatitis virus infection, replication is normally maintained by a population of episomal covalently closed circular (ccc) viral DNA molecules in the hepatocyte nuclei. These molecules have a limited half life and do not replicate in the nucleus. Therefore, natural host hepatocytes are capable of being completely "cured" of viral DNA. Thus, it would be highly desirable to obtain a system whereby this characteristic of natural host cells could be employed in antiviral testing, since a complete "cure" is possible and could be screened for.

Recently, advances have been made in mouse liver repopulation with transplanted rat hepatocytes (15). In addition, a hepatocyte-lethal phenotype has been discovered in urokinase-type plasminogen activator (uPA) transgenic mice and such mice have been shown to be capable of liver replacement with xenografted rat hepatocytes (16, 17, 18). Such replacement of the mouse liver with xenogenic rat hepatocytes is facilitated in a uPA mouse because uPA transgene expression places these hepatocytes at a growth disadvantage compared with nontransgenic hepatocytes (16). Transplanted hepatocytes in this system are thus selectively amplified in a mixed polyclonal pattern. A disadvantage of this system is that the rat cells are not natural hosts for hepadnaviruses and cannot be infected by natural mechanisms with any of the known hepadnaviruses. It would thus be advantageous to have a method for repopulating the liver parenchyma of many mice with xenogenic mammalian hepatocytes capable of being infected with hepadnaviruses and derived from a single donor, thus creating mice with chimeric livers that contain genetically identical hepatocytes.

The recent isolation of a Severe Combined Immune Deficiency (SCID) mouse which is homozygous for the Recombination Activation Gene 2 (RAG2) knockout mutation provides a mouse deficient in both B and T immune cells (22). This immunetolerant mouse is not capable of rejecting xenogenic tissue.

The woodchuck animal model provides for the study of woodchuck hepatitis virus (WHV) infection in a natural host setting which mimics infection of human liver with HBV (19, 20, 21). One disadvantage of the woodchuck is that it is a relatively inaccessible, genetically heterogeneous animal which is difficult to breed and maintain in a laboratory setting. It would be highly desirable to obtain a model system for hepadna and other hepatitis viral infection in an animal that is both easy to breed and maintain, as well as being genetically controlled and cost effective.

It would be highly desirable to obtain a convenient animal model system for the observation of hepatitis virus replication and development in host hepatocytes that can be infected by natural means. Indeed, it would be highly desirable to use the above model to test the effects of drugs potentially active against hepatitis virus replication, development of hepatocellular carcinoma and treatments for such. A variety of treatments for diseases resulting from hepatitis virus infection could be tested in such an animal model system.

SUMMARY OF THE INVENTION

In one aspect, the invention provides a method of making a chimeric mouse by creating an immunetolerant mouse which has a degenerated liver, and repopulating the degenerated liver parenchyma by transplanting xenogenic mammalian hepatocytes capable of growing and being infected with at least one compatible mammalian hepatitis virus.

The xenogenic mammalian hepatocytes used to repopulate the chimeric mice can be infected prior to their use in transplantation or following repopulation.

A further aspect of the invention provides a chimeric mouse model system comprising an immunetolerant mouse which has a degenerated liver repopulated with xenogenic hepatocytes capable of growing and being infected with compatible mammalian hepatocytes.

In yet another aspect, the invention provides a method for screening anti-viral activity of a test compound comprising administering said test compound to the chimeric mouse of the invention which has been infected with at least one compatible mammalian virus and assaying the level of replication of the virus in said mice.

A still further aspect of the invention provides a method for screening anti-cancer activity of a test compound comprising administering said test compound to the chimeric mouse of the invention which has been infected with at least one compatible mammalian hepatitis virus and assaying the mice for the development of hepatocellular carcinoma in said mice.

A preferred immune tolerant mouse with degenerated liver is hemizygous or homozygous for the urokinase-type plasminogen activator (uPA) transgene and is homozygous for the Recombination Activation Gene 2 (RAG-2) knockout gene. Such a mouse is herein designated as a uPA/RAG2 mouse. A preferred xenogenic hepatocyte is a woodchuck hepatocyte and a preferred compatible hepatitis virus is the Woodchuck Hepatitis Virus (WHV).

A particularly preferred xenogenic hepatocyte is a primate hepatocyte and a particularly preferred compatible hepatitis virus is the human hepatitis A virus, human hepatitis C virus, human hepatitis D virus coinfected with hepadnavirus, human hepatitis E virus, human hepatitis F virus or human hepadnavirus.

BRIEF DESCRIPTION OF THE DRAWINGS

The file of this patent contains at least one drawing executed in color. Copies of this patent with the color drawing(s) will be provided by the Patent and Trademark Office upon request and payment of the necessary fee.

FIG. 1 is a photograph depicting the migration pattern of mouse (lane 1) and woodchuck (lane 2) serum albumin in a Coomassie Blue stained gel. Serum from a chimeric uPA/RAG-2 mouse containing woodchuck hepatocytes is shown in lane 3. Bands in the position of both mouse and woodchuck albumin are a diagnostic marker for the presence of functional woodchuck hepatocytes in the chimeric mouse.

FIGS. 2(A)–(E) comprise photographs of gels that depict the presence of woodchuck genomic DNA and WHV DNA plus the WHV X (WHx), Core (WHc) and envelope (WHs) proteins in the liver of uPA/RAG-2 mice transplanted with WHV-positive woodchuck hepatocytes. FIG. 2(A) depicts a Southern blot of chimeric mouse liver genomic DNAs hybridized with a woodchuck genome DNA probe. FIG. 2(B) depicts a Southern blot showing WHV DNA forms, detectable in uPA/RAG-2 mouse genomic liver DNA, hybridized with a WHV DNA probe. FIG. 2(C) depicts a Western blot of uPA/RAG2 chimeric mouse liver extracts detection. WHx using, an anti-WHx antibody. FIG. 2(D) As in 2(C) but detecting WHc using an anti-WHc antibody. FIG. 2(E) As in 2(C) but detecting WHs using an anti-WHs antibody.

FIG. 3(A) depicts detection of WHcAg in a uPA/RAG-2 mouse liver containing WHV-positive woodchuck hepatocytes by immunostaining with a WHc-antiserum. Woodchuck hepatocytes infected with WHV have specific red immunoflourescent signals not present in mouse cells.

FIG. 4 is a graph depicting the effect of interferon-alpha and dexamethasone upon the titer of WHV in the blood of chimeric uPA/RAG-2 mice transplanted with woodchuck hepatocytes.

FIGS. 5(A), 5(C), 5(E), and 5(G) depict staining of livers from a donor woodchuck. FIGS. 5(B), 5(D), 5(F), and 5(H) depict staining of liver sections from a UPA/RAG-2 chimeric mouse after repopulation with WHV-positive woodchuck hepatocytes from the donor woodchuck liver depicted in 5A, C, E, and G.

FIG. 6(A) depicts a Southern blot analysis of DNA of a tumor which developed in a uPA/RAG-2 chimeric mouse liver. The tumor DNA hybridized with both a woodchuck genomic DNA probe (lane 3) and a viral WHV DNA probe(lane 4).

DETAILED DESCRIPTION

Figure 2B:
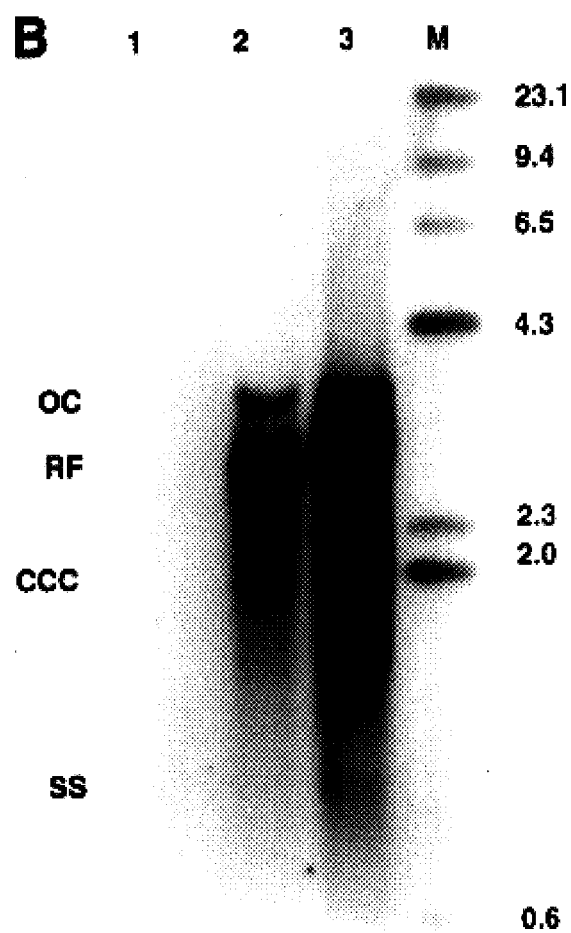

The present invention provides a chimeric mouse liver model system for mammalian hepatitis. The chimeric mouse liver model is for use in studying hepadnavirus (hepatitis B virus) infection, as well as other hepatitis virus infection and in developing methods for preventing and treating diseases developing from such infection.

The chimeric mice of the invention are generated by repopulating the degenerated liver parenchyma of immune-tolerant mice by transplanting xenogenic mammalian hepatocytes capable of being infected with at least one compatible mammalian hepatitis virus. When used as a model system for hepatitis, the xenogenic mammalian hepatocytes can be infected prior to transplantation or following repopulation.

"Degenerated liver" as used herein is a diseased liver having compromised biochemical function which leads to either hepatocyte death and/or an inability to replicate. Mouse genes or mutations which lead to a degenerated liver include, but are not limited to, the presence of the uPA transgene and to limitations in the uPA gene.

Chimeric as used herein is the transplanted degenerated mouse liver which is composed of parts that are of different origin from the native mouse liver cells. "Immunetolerant" as used herein is defined as an animal such as a mouse which is deficient in B and T cells. Examples of mice which are immunetolerant are nude mice, RAG2 knockout mice, RAG1 knockout mice, and SCID mice.

"Transplanting" as used herein is the process of transferring isolated xenogenic mammalian liver derived cells into the immunotolerant mouse which has a degenerated liver. Said liver cells consist of a great majority (generally greater than 75%) of primary hepatocytes. Other cells which are transplanted along with the hepatocytes may include endothelial cells, ito cells and kupfer cells.

"Repopulating" as used herein is the process by which the transplanted liver cells are incorporated into the recipient liver parenchyma and grow, replacing the native degenerated host liver parenchyma.

Xenogenic mammalian hepatocytes can be transplanted into degenerated mouse livers via a number of methods. These include splenic injection or direct portal vein injection. A preferred method of transplantation is via splenic injection (15). Transplanted hepatocytes grow as microclones in the recipient liver from a common donor source and their growth pattern generally restores a normal cord structure in the liver.

The xenogenic mammalian hepatocytes of the invention can be derived from any desired source because the immunetolerant mouse will have no B and T cells and are incapable of eliciting an immune response to xenogenic cells. Sources for xenogenic mammalian hepatocytes for use in the present invention include, but are not limited to, human, chimpanzee, baboon, woolly monkey, ground squirrel, and woodchuck hepatocytes. Preferred xenogenic mammalian hepatocytes of the invention are hepatocytes from the woodchuck (i.e., *Marmotta monax*).

Particularly preferred xenogenic hepatocytes of the invention are primate hepatocytes selected from the group consisting of human, chimpanzee, baboon and hepatocytes isolated from primates capable of supporting the replication of human hepatitis viruses.

The xenogenic mammalian hepatocytes of the invention can be infected with at least one compatible mammalian virus.

The xenogenic primate hepatocytes of the invention can be infected with at least one compatible human hepatitis virus.

"Compatible" as used herein refers to any virus which is capable of replicating and developing in the xenogenic mammalian hepatocytes. Examples of compatible mammalian viruses include, but are not limited to, hepatitis A virus, hepatitis C virus, hepatitis delta virus coinfecting with hepadnavirus, hepadnavirus (hepatitis B virus), human hepatitis B virus, ground squirrel hepatitis virus, woodchuck hepatitis virus, hepatitis E virus and hepatitis F virus.

Particularly preferred compatible hepatitis viruses are human hepatitis viruses, including, but not limited to human hepatitis A virus, human hepatitis B virus and human hepatitis C virus, human hepatitis delta virus coinfecting with hepadnavirus, human hepatitis E virus and human hepatitis F virus.

When woodchuck hepatocytes are used as the xenogenic mammalian hepatocytes, woodchuck hepatitis virus (WHV) replication is supported indefinitely.

Examples of mammalian hepadnavirus and hepatocyte combinations can be found in Table 1.

TABLE 1

Mammalian Hepadnaviruses and Their Hosts

| Virus | Natural Host | Other Hosts and Cells to be Infected |
|---|---|---|
| Hepatitis B (HBV) | Human | Chimpanzee, baboon, HepG2 and Huh7 Hepatocellular carcinoma cells |
| Woodchuck Hepatitis (WHV) | Woodchuck (*Marmotta Momax*) | Ground squirrel |
| Ground Squirrel Hepatitis (GSHV) | Ground Squirrel | Woodchuck |
| Wooly Monkey Hepatitis (WMHV) | Wooly Monkey | NOT AVAILABLE |

A preferred chimeric mouse of the invention is generated by repopulating the degenerated liver parenchyma of an immunetolerant mouse which is hemizygous or homozygous for the urokinase-type plasminogen activator (uPA) transgene and is homozygous for the Recombination Activation Gene 2 (RAG-2) which is a knockout gene.

The RAG2 mice are immunotolerant because they lack the ability to produce mature, functional B or T cells. The expression of the uPA transgene in the native hepatocytes of the uPA transgenic mice causes them to undergo pathological changes involving alterations of their membranes which block important metabolic functions and block their cell division. These alternations cause a great many hepatocytes to die. This pathology is due to an excessive amount of uPA production by the hepatocytes, however, the uPA produced in these mouse hepatocytes does not block the growth of transplanted hepatocytes which do not contain the transgene.

The liver parenchyma of the uPA/RAG-2 mouse is repopulated with xenogenic mammalian hepatocyte such that the liver containing the xenogenic cells is chimeric. This chimeric uPA/RAG2 mouse can then be infected with compatible mammalian hepatitis virus.

The uPA/RAG-2 mice are generated by:

a. crossing a hemizygous or homozygous urokinase-type plasminogen activator (uPA) transgenic mouse with a homozygous Recombination Activation Gene 2 (RAG-2) knockout mouse to generate F1 uPA hemizygous, RAG-2 hemizygous sibling mice; and b. crossing F1 sibling mice to each other in sibling matings or backcrossing the F1 mouse to a RAG2 homozygote, to generate F2 uPA hemizygous or homozygous, RAG2 homozygous (uPA/RAG2) mice.

F2 mice can also be sibling mated to generate additional uPA/RAG2 F3 mice.

Following transplantation, the xenogenic mammalian hepatocytes repopulate the degenerated uPA/RAG-2 liver parenchyma, and become integrated into it, replacing up to 90% of the uPA/RAG-2 mouse hepatocytes.

The chimeric mouse model system of the invention makes it possible to study hepatitis virus replication both in rapidly proliferating hepatocytes during liver repopulation and in quiescent hepatocytes after completion of liver regeneration. The chimeric mouse system combines several desirable characteristics of previous animal models for studying hepatitis virus infection and pathogenesis.

The chimeric mice of the invention also provide a system in which to study mechanisms of viral persistence in natural host hepatocytes in the absence of B and T cell-mediated immune responses. The absence of B and T cells in these mice provides for immune tolerant mice which do not develop liver disease upon infection with hepatitis virus. The absence of B and T cells, and thus immune responses, in these mice provides a system whereby the liver is not degraded or degenerated upon infection. The system thus makes it possible to test compounds which inhibit viral replication in a controlled environment, in the absence of actual liver disease.

The absence of B and T cells in the chimeric mice of the invention also provides an opportunity for their replacement with specific xenogenic or mouse immune system cells selected for specific B or T cell functions. The xenogenic cell type is selected based upon the type of xenogenic mammalian hepatocytes with which the chimeric mice are repopulated. If woodchuck cells are the donor cells then woodchuck or mouse immune system cells are selected.

When the xenogenic mammalian hepatocytes have been infected with compatible mammalian hepatitis virus, the chimeric mouse model system of the invention can be used to study the replication of hepatitis virus and the development of hepatocellular carcinoma (HCC) disease states. The infected chimeric mice also provide a system in which to monitor the effects of antiviral and anticancer drugs. The mice can be used in a method to screen and identify treatments for chronic hepatitis virus infection in mammals by evaluating the efficacy of drugs which effect replication. The mice can also be used in a method to screen and identify chemotherapeutic treatments for malignant hepatic cancers and precancerous tissue in such mice, as well as in a method to screen for anticancer agents which prevent the development of hepatocellular carcinomas in such mice.

The development of hepatocellular carcinoma progresses from normal hepatocytes through a number of stages. These include 1) precancerous hyperplasia where the cells exhibit extra growth; 2) altered hepatic foci, where precancerous lesions are amplified; 3) neoplastic nodules; 4) adenoma or benign tumors which at late stages may exhibit early malignancy; and 5) malignant cancerous tumors or hepatocellular carcinomas.

The basic steps in using this model to test antiviral compounds include (1) characterizing the level of hepadnavirus DNA in the blood of the mouse before treatment begins; (2) injecting various doses of the test compound into the mouse (intraperitoneally, intramuscularly or intravascularly) at various intervals (daily, weekly etc); (3) analyzing the blood of the mice for a reduction in viral titre; (4) analyzing the liver of the mice for curing or reduction of the viral DNA (ie. removal of viral closed circular covalent DNA); (5) ceasing treatments and determining if there is a recurrence of viral replication.

Antiviral agents can be tested in the chimeric mouse model system of the invention for their effectiveness in clearing molecular species of hepatitis viral DNA. Among the antiviral agents that can be tested in the mouse model of the invention are the interferons ($\alpha$, $\beta$, $\gamma$, etc.), cytokines interferons, tumor necrosis factor alpha, FN, F$\alpha$, IL1–13, etc.), all growth factors (TGF$\beta$, EGF, TGF$\alpha$, etc.), hormones (glucocorticoids, insulin, growth hormone, etc.), nucleoside analogues (3TC, etc.), and antisense DNA/RNA. However, the system is not limited to testing these agents and virtually any agent believed to have antiviral activity can be tested with the chimeric mouse model system of the invention.

In addition to testing the antiviral agents, in the chimeric mouse model system of the invention, these agents can also be also tested as anticancer agents. However, the system is not limited to testing these agents and virtually any agent believed to have anticancer activity can be tested with the chimeric mouse model system of the invention. Tests for the activity of anticancer agents are carried out similarly to those for anti-viral testing, except that for testing the prevention of cancer, the mice are allowed to live a longer time, (up to a year or two) in order to observe the occurrence of cancer. In addition, treatment with the potential anti-cancer drug would be discontinued in some animals to determine whether there was reoccurrence of the tumor. Tests for chemotherapeutic agents would be carried out as above, except that mice with malignant cancerous tissue (i.e., tumors) or precancerous tissue would be used and the amelioration of the malignant cancerous tissue or the prevention of the development of cancerous tissue from precancerous tissue is monitored.

In all of the tests for antiviral or anti-cancer compounds, control mice are used for comparison. Control mice are those that are identical to test mice except that no compounds are administered.

A major objective for hepatocarcinogenesis studies is to define the cellular and molecular phenotype of precancerous hepatocytes in order to design early diagnostic and intervention protocols. The straightforward identification of amplified precancerous lesions called altered hepatic foci (AHF), provides a tool for studying genetic changes in hepatocytes derived from precancerous lesions. Such identification can be carried out through analysis and identification of unique hepatocyte phenotypes present in AHFs. The AHF hepatocytes have large nuclei and prominent nucleoli. The clonality and origin of the lesions can be determined through analysis of viral DNA integration patterns in both the donor mammalian liver and in the transplanted mammalian hepatocytes in the chimeric mouse liver. In addition, the clonal potential of donor liver tumor cells derived from chronic hepatitis virus carrier donors can be determined in the chimeric mice.

The presence of unique hepatitis virus DNA integrations in HCCs which arise in the chimeric mouse liver demonstrates that an in vivo selection and clonal expansion of the xenogenic mammalian hepatocytes has taken place. This activity suggests that tumor progression occurs following cell transplantation. Such clonal expansion of the xenogenic mammalian hepatocytes provides sufficient quantities of transformed cells to investigate and better understand the roles of viral genes and hepatitis virus DNA integrations in the multistep progression to HCC and can be applied to the analysis of any type of xenogenic mammalian hepatocyte/ compatible mammalian hepatitis virus combination of the invention.

The following examples are intended to illustrate but not limit the present invention.

EXAMPLE 1

Generation of Chimeric Mice

Animals uPA mice were obtained from Jackson Laboratories (Bar Harbor, Me.), RAG-2 knockout mice from Taconic Farms (Germantown, N.Y.), and adult woodchucks from either North Eastern Wildlife (South Plymouth, N.Y.), or Cornell University (Ithaca, N.Y.). Animals were housed and maintained under specific pathogen-free conditions in accordance with NIH guidelines. One uninfected woodchuck was utilized, which was negative for all WHV markers, and three infected woodchucks were utilized which all had persistent WHV infections and were woodchuck hepatitis virus surface antigen (WHsAg) and anti-woodchuck hepatitis virus core antibody (anti-WHc) positive.

Generation of Tolerant uPA/RAG-2 Mice

Hemizygous urokinase-type plasminogen activator (uPA) transgenic mice were crossed with homozygous Recombination Activation Gene 2 (RAG-2) knockout mice to generate F1 uPA hemizygous, RAG-2 hemizygous sibling mice. These F1 sibs were then backcrossed to homozygous RAG2 knockout mice to generate F2 uPA hemizygous or homozygous, RAG2 homozygous (uPA/RAG2) mice for use in hepatocyte transplantation/liver repopulation experiments. In addition, the F1 mice were, in some cases, sibling mated to derive the desired uPA/RAG2 F2 mice. The F2 sibs were also backcrossed to generate additional uPA/RAG2 F3 mice.

The uPA transgene was identified by polymerase chain reaction (PCR) of mouse-tail DNA with the following nucleotide sequences: Primer 1: 5'-CATCCCTGTGACCC CTCC-3' (SEQ ID NO. 1), Primer 2: 5'-CTCCAAACC ACCCCCCTC-3' (SEQ ID NO. 2). Homozygous uPA transgenic mice were distinguished from hemizygous mice by PCR as previously reported (18). For the embodiments described herein, both homozygous and hemizygous uPA mice were used. The RAG-2 knockout mutant gene was identified by PCR analysis of in tail DNA as previously described (23).

Isolation and Transplantation of Woodchuck Hepatocytes

WHV-infected woodchuck hepatocytes were isolated by the two-step in situ collagenase perfusion method followed by differential centrifugation (24). Hepatocyte viability was >95% as measured by trypan blue dye exclusion. From $5 \times 10^5$ to $1 \times 10^6$ hepatocytes were transplanted into a number of 10–18 day old uPA/RAG-2 mice by intrasplenic injection (24).

Repopulation with uninfected woodchuck hepatocytes is described in detail in Example 10 below.

EXAMPLE 2

Screening for Normalized Serum Markers in Mice with Transplanted Hepatocytes

To screen for the survival and growth of the transplanted woodchuck hepatocytes, sera of mice which received transplanted hepatocytes were analyzed for total protein, albumin, bilirubin, alanine aminotransferase activity (ALT), and aspartate aminotransferase activity (AST) in a standard automated clinical analyzer (Technicon Chem-1, San Francisco, Calif.). Normal serum markers in transplanted mice would indicate that the transplanted hepatocytes had restored normal liver function to the uPA/RAG2 mice.

Recipient and control mice were tested. Fifty milliliters of blood was collected from the retroorbital orifice and this was allowed to coagulate. Serum was extracted and injected directly into the automated analyzer to determine values. The blood markers of uPA/RAG-2 mice with chimeric livers containing woodchuck hepatocytes were found to be similar as compared to control uPA/RAG-2 mice without woodchuck hepatocytes (Table 2).

TABLE 2

Serum Parameters in uPA/RAG2 Mice

| Mouse Colony Accession Number | 351 | 457 | 496 | 969 |
|---|---|---|---|---|
| Woodchuck Hepatocytes | [−][1] | [−] | [+][2] | [+] |
| Total Protein (g/dl) | 4.4 | 4.0 | 4.6 | 4.2 |

TABLE 2-continued

Serum Parameters in uPA/RAG2 Mice

| Albumin (g/dl) | 2.6 | 2.4 | 2.8 | 2.6 |
|---|---|---|---|---|
| AbT (u/l) | 118 | 104 | 112 | 124 |
| AST (u/l) | 140 | 124 | 139 | 154 |
| Bilirubin (mg/dl) | 0.2 | 0.2 | 0.3 | 0.2 |

[1][−]Denotes no transplantation
[2][+]Denotes transplantation with xenogenic woodchuck hepatocytes In addition, partial hepatectomies in chimeric mice were performed under tribromoethanol-anesthesia (Aldrich, Milwaukee, Wis.) with approved protocols (25). The uPA/RAG-2 mice with chimeric livers containing woodchuck hepatocytes were clinically healthy and the livers appeared normal in respect to color, size, and liver weight to body weight ratios at sacrifice.

EXAMPLE 3

Detection of Woodchuck and Mouse Albumin in Serum

The presence of serum albumin was tested as follows: 5 μg of total serum proteins were solubilized (26), boiled, and subjected to electrophoresis through an SDS-PAGE. Proteins resolved in 7.5% gels were fixed and stained with Coomassie Blue. SDS-PAGE showed that mouse and woodchuck serum albumin migrated differently (FIG. 1). In chimeric uPA/RAG-2 mice, three months after woodchuck hepatocyte transplantation, this assay demonstrated the presence of both woodchuck and mouse serum albumin.

EXAMPLE 4

Measurement of Woodchuck Hepatocyte Repopulation

To directly demonstrate the presence of woodchuck hepatocytes in chimeric uPA/RAG-2 mouse livers, DNAs extracted from recipient livers were hybridized with a total woodchuck genomic probe which detects only highly repeated sequences in the woodchuck genome (FIG. 2A). Genomic DNAs were extracted from frozen liver and used for Southern blot analysis as previously described (27, 28). For detecting woodchuck genomic DNA in transplanted uPA/RAG-2 mouse livers, 150 ng (Pvu II digested) woodchuck DNA was used for a $^{32}$P-labeled random genomic probe. Blots were hybridized under high stringency conditions (29) at 45° C. for 2 hrs. To estimate the extent of uPA/RAG-2 mouse liver repopulation with woodchuck hepatocytes, we hybridized test mixtures of woodchuck and mouse genomic DNAs in various proportions as controls (FIG. 2A, lanes 1–5). Lanes 1–4 present mixtures of genomic woodchuck liver DNA and untransplanted uPA/RAG-2 mouse genomic liver DNA with signals reflecting: 100%, 50%, 20%, and 1%, woodchuck hepatocyte DNA, respectively. Lane 5 shows 100% (untransplanted) uPA/RAG-2 mouse DNA. Lane 6 shows that woodchuck DNA was undetectable in the spleen of transplanted uPA/RAG-2 mice.

DNAs from five liver lobes of a chimeric uPA/RAG-2 mouse transplanted with WHV-positive woodchuck hepatocytes (#496) showed the presence of WHV DNA in varying amounts. (FIG. 2A, lanes 7–11). The data show that transplanted woodchuck hepatocytes were present in abundance in all liver lobes varying from approximately 30% to >95%.

EXAMPLE 5

WHV DNA Replication and Persistence in Chimeric Mouse Liver

Chimeric mice transplanted with WHV-positive woodchuck hepatocytes were tested to determine if the repopulated livers supported WHV replication. Total genomic liver DNA of a representative chimeric recipient mouse repopulated with WHV infected woodchuck hepatocytes (#496) was analyzed for WHV DNA by hybridizing a Southern blot with a genome length 3.3 kb WHV-DNA $^{32}$P-labeled probe (29). Lane 1 shows control non-transplanted uPA/RAG-2 mouse liver DNA; lane 2 shows DNA from a chimeric uPA/RAG-2 mouse liver transplanted with WHV-positive woodchuck hepatocytes; and lane 3 shows DNA from the donor woodchuck liver. Open circular (OC) WHV DNA, replicative DNA forms (RF), and covalently closed circular (CCC) WHV DNA match the profile of WHV DNA from the donor woodchuck (#2765) (FIG. 2B, lanes 2 and 3). SS is single stranded DNA.

EXAMPLE 6
Detection of WHx and WHc Proteins in Chimeric Mice

Woodchuck hepatitis virus protein WHx was immunoprecipitated from liver extracts with a rabbit WHx antiserum and subjected to sodium dodecyl sulfate (SDS)-polyacrylamide gel electrophoresis (PAGE) as previously described (30). For the detection of WHV core protein, 20 µg of total cell extracts were solubilized (26), boiled, and separated by SDS-PAGE.

Transblots of the SDS-PAGEs were probed with either WHx-antiserum (1: 1,000 dilution) or WHc-antiserum (1:5,000 dilution) and binding was detected by the enhanced chemiluminescence (ECL) system (30) (Amersham. Arlington Heights, Ill.).

Figure 2C:
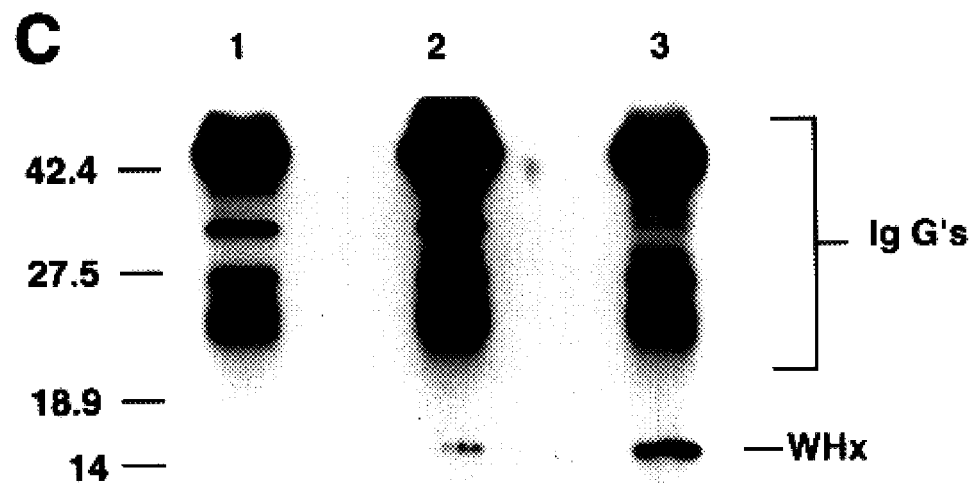

WHx proteins were present in chimeric mouse #496 liver. FIG. 2C shows uPA/RAG-2 mouse liver (lane 1); chimeric uPA/RAG 2 mouse liver transplanted with WHV-positive woodchuck hepatocytes (lane 2); and donor woodchuck liver (lane 3).

Figure 2D:
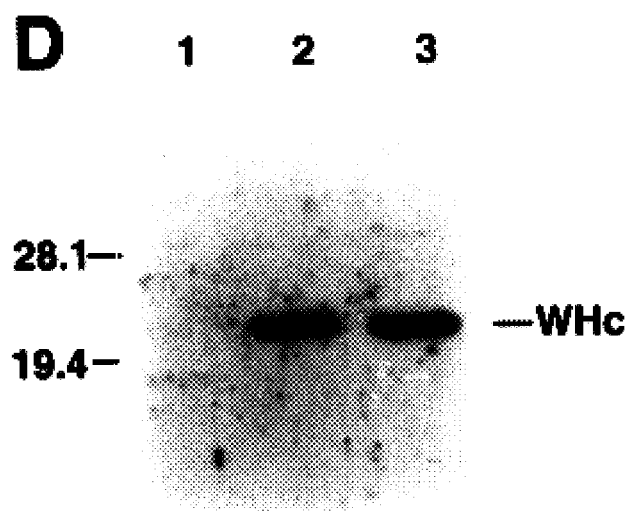

WHc proteins were also present in chimeric mouse #496 liver. FIG. 2D shows uPA/RAG-2 mouse (lane 1); chimeric uPA/RAG-2 mouse transplanted with WHV-positive woodchuck hepatocytes (lane 2); and donor woodchuck (lane 3).

EXAMPLE 7
Detection of WKsAg in Woodchuck and uPA/RAG-2 Mouse Sera

Figure 2E:
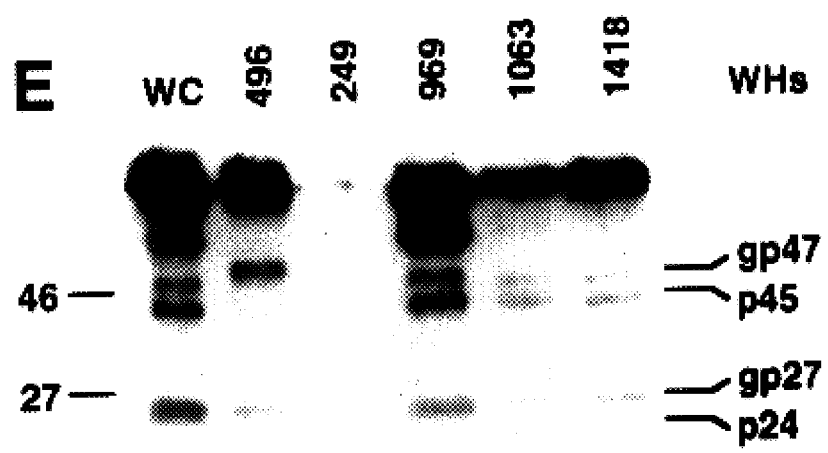

Mouse serum was tested for the presence of WHsAG. For immunoblotting of WHsAg, proteins were resolved in SDS-PAGE, electrotransferred, probed with a rabbit antiserum against WHsAg (WHs-antiserum) (1:1,000 dilution), and visualized by ECL. FIG. 2E shows immunoblotting with WHs-antiserum of uPA/RAG-2 mouse sera (#249), uPA/RAG-2 mouse sera transplanted with WHV-positive woodchuck hepatocytes (#496, 969, 1063, 1418). Lane 1: WHV-positive woodchuck serum.

EXAMPLE 8
WHV RNA Detection

Analysis of WHV RNA in chimeric mouse #496 liver was analyzed by Northern blot performed using 15 ug of total RNA from the mouse #496 liver RNA. The blot was hybridized with a $^{32}$P total WHV, DNA genome probe. The blot revealed the expected major mRNA species of 3.6 and 2.4 Kb corresponding to the pregenome mRNA and the major envelope protein RNAs.

EXAMPLE 9
Histological Studies

Serial cryostat sections of the chimeric uPA/RAG-2 mouse livers repopulated with WHV infected woodchuck hepatocytes, as well recipient uPA/RAG-2 mice without transplants, were examined by hematoxylin & eosin (H&E) staining, dipeptidyl peptidase IV (DPPIV) enzyme activity (31) and immunohistochemistry with a rabbit WHc-antiserum against woodchuck hepatitis core antigen (WHcAg). To investigate the growth pattern of woodchuck hepatocytes in uPA/RAG-2 mouse liver, we performed immunohistochemistry using an antibody directed against WHV core antigens (anti-WHcAg).

For immunolabeling, sections were fixed in 4% paraformaldehyde, incubated with WHc-antiserum (diluted 1:250 in PBS containing 5% sheep serum) at room temperature and subsequently incubated with the Cy3-conjugated sheep anti-rabbit IgG antibody (Sigma, St. Louis, Mo.) diluted 1:200 in phosphate buffered saline (PBS) with 5% sheep serum at room temperature. Finally, slides were mounted in 40 mg n-propylgallate/ml in 90% glycerol, 10% 0.5 M sodium carbonate. pH 8, for viewing under a fluorescence microscope.

Figure 3A:
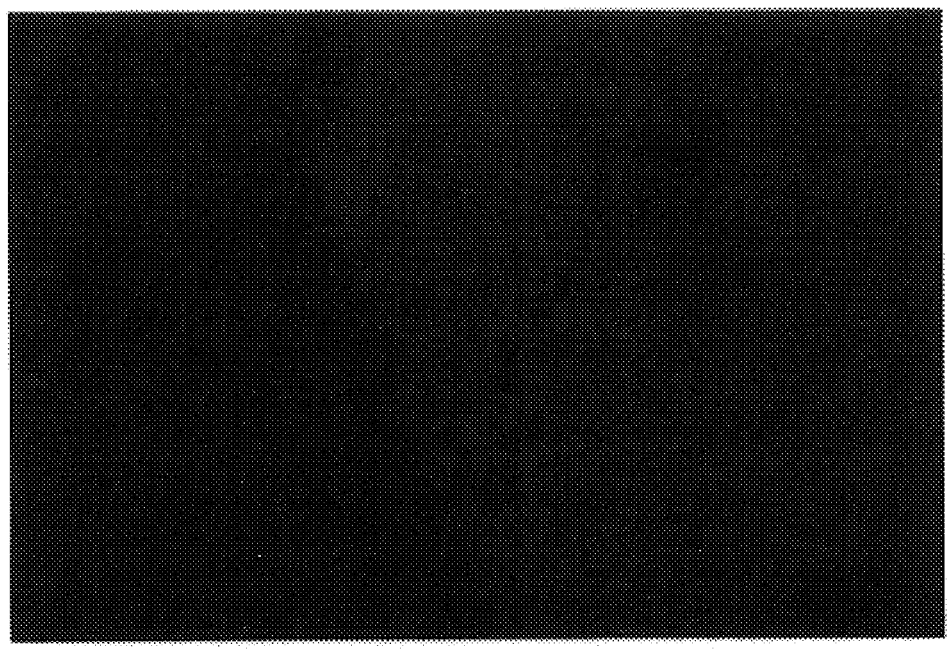
FIGS. 3(A) and (B) comprise photographs which depict histological studies of cryostat sections from WHV-infected chimeric mice.

WHV-positive woodchuck hepatocytes had seeded the liver and grown in a nodular pattern within the framework of the preexisting liver with maintenance of the liver cord structure as can be detected by the specific red fluorescence staining signal in the chimeric liver (FIG. 3A). A nodule containing transplanted WHV-positive woodchuck hepatocytes (lighter area, rhodamine light) and host mouse hepatocytes that presumably deleted the uPA transgene (darker stained area) (200x). Untransplanted mice did not show any positive staining.

Figure 3B:
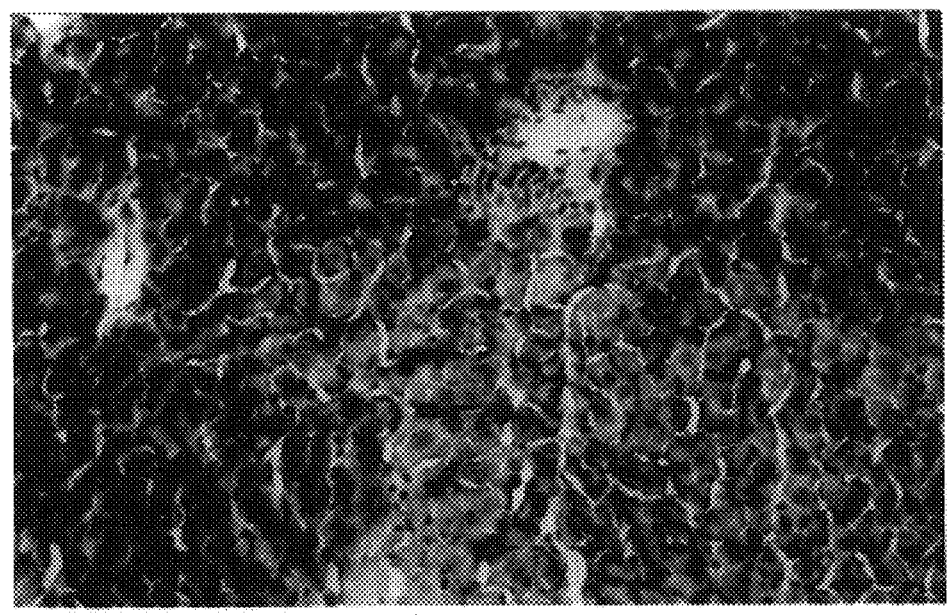
FIG. 3(B) depicts DPPIV staining of bile canaliculi (200×) in uPA/RAG-2 mouse liver containing woodchuck hepatocytes.

Integration of the woodchuck hepatocytes into the liver architecture was evaluated by histochemistry for the enzyme DPPIV which is localized in bile canaliculi of hepatoqytes (31). Mouse hepatocytes appeared smaller and DPPIV-positive areas were therefore more compact. In contrast, areas containing woodchuck cells showed greater spacing between DPPIV-positive domains due to larger cell sizes. In chimeric uPA/RAG-2 mouse livers containing woodchuck and mouse hepatocytes we observed networks of DPPIV positive bile canaliculi between adjacent mouse and woodchuck hepatocytes (FIG. 3B). Bile canaliculi (200x) are visible between mouse hepatocytes (darker staining) and transplanted woodchuck hepatocytes (lighter staining). Nuclei are counterstained with hematoxilin. The presence of woodchuck hepatocytes in those sections was confirmed by performing immunohistochemistry using a WHc-antiserum in serial sections from uPA/RAG-2 mouse liver tissues.

Interestingly, despite expression of WHV proteins in transplanted woodchuck hepatocytes, we did not observe any hepatocellular infiltration with inflammatory cells. The uPA/RAG-2 mice are of course deficient in T and B lymphocytes, however, no evidence was found of infiltration with granulocytes or macrophages.

EXAMPLE 10
Detection of WHV DNA in Serum

Woodchucks were anesthetized with ketamine (Fort Dodge Laboratories, Fort Dodge, Iowa) and xylazine (Bayer, Shawnee Mission, Kans.) and blood was collected from the femoral vein. Blood was drawn from the tail vein in mice and woodchuck and mouse sera were dot blotted onto a nylon membrane (32), hybridized with a $^{32}$P-labeled WHV-DNA probe (29) and the number of WHV DNA molecules were quantitated by scanning densitometry. Serial dilutions of known amounts of a plasmid containing one copy of WHV DNA served as a standard.

Figure 4:
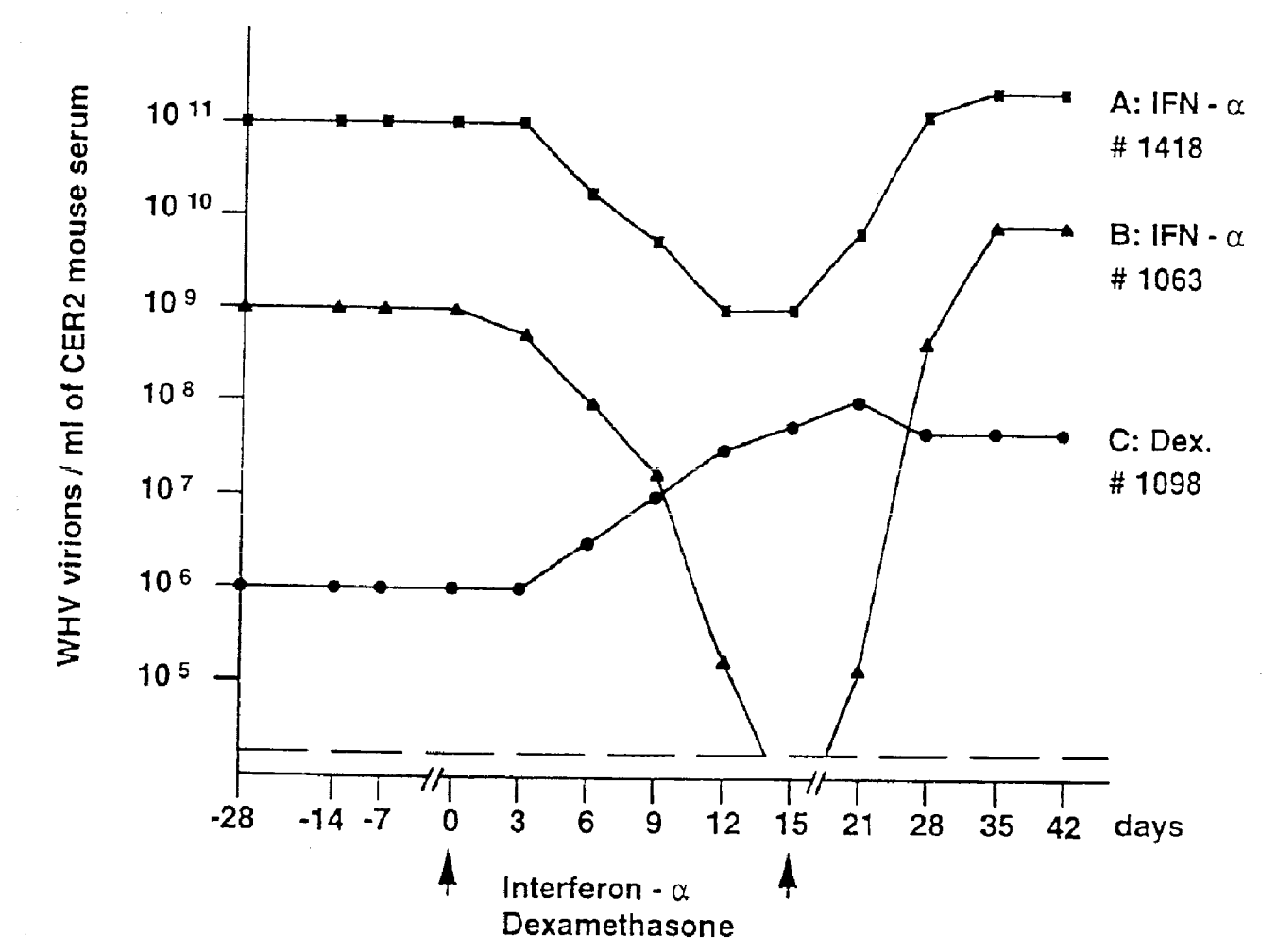

WHV DNA in the serum of chimeric uPA/RAG-2 mice repopulated with infected woodchuck hepatocytes became detectable only after completion of liver regeneration with a lag period of viremia of 8–12 weeks after transplantation. WHV DNA titers stabilized at a level of approximately $5\times10^8$ viral genomes per ml in the transplanted mouse #496 as compared to $1\times10^9$ WHV genomes per ml in the donor woodchuck (data not shown). In other chimeric uPA/RAG-2 mice, WHV titers of up to $1\times10^{11}$ virions/ml mouse serum were detected (FIG. 4). Each line in the Figure shows individual uPA/RAG-2 mice containing WHV-secreting woodchuck hepatocytes. Black arrows mark starting point and withdrawal of agents. Time points mark the collection of serum samples. The dashed line represents the threshold of sensitivity for the Dot blot analysis.

In virus particles isolated from the serum of transplanted uPA/RAG-2 mice, viral DNA could be isolated and it migrated on Southern blots in a similar fashion to the WHV DNA from the donor woodchuck.

EXAMPLE 11

Infection of Naive, Uninfected Woodchuck Hepatocytes in Chimeric Mice

To investigate whether naive woodchuck hepatocytes could be infected with WHV in uPA/RAG-2 mice, hepatocytes from an adult uninfected woodchuck were transplanted into the liver of uPA/RAG-2 mice according to the methods of Example 1. After completion of liver regeneration, three months following transplantation, four chimeric uPA/RAG-2 mice were subjected to a liver biopsy and the presence of woodchuck hepatocytes was confirmed by Southern blot analysis according to the methods of Example 1.

Subsequently, these chimeric UPA/RAG-2 mice were infected with either 10 μl i.m. of a WHV-positive woodchuck serum, containing approximately $1\times10^9$ virions/ml, or with 10 μl i.m. of WHV containing serum from uPA/RAG-2 mouse #496 ($5\times10^8$ virions/ml). The establishment of productive infection was monitored by serum dot blot analysis for WHV DNA. WHV DNA became detectable at four weeks after infection. Southern blot analysis of chimeric uPA/RAG-2 mouse liver DNAs hybridized with a WHV DNA genomic probe demonstrated the presence of open circular and replicative WHV DNA forms. The serum WHV virion levels have remained stable for an additional ten months in the infected animals confirming the persistence of WHV infection in chimeric uPA/RAG-2 mice wherein the hepatocytes were infected after transplantation.

EXAMPLE 12

Antiviral Studies in WHV Replicating Chimeric uPA/RAG-2 Mice

To confirm the usefulness of the chimeric uPA/RAG-2 mouse model for studying hepadnaviral replication, modulation of WHV replication with either interferon-alpha or dexamethasone treatment was investigated. Three chimeric uPA/RAG-2 mice were chosen for this experiment, #1418 contained hepatocytes from a chronic WHV carrier, while mice #1063 and #1098 were transplanted with naive woodchuck hepatocytes and infected with WHV-containing sera as described in Example 11. All mice showed a constant level of viral replication before drug administration (See FIG. 4).

In order to test the effects of antiviral compounds on the replication of WHV DNA in infected livers, 135 IU/g body weight of Interferon-alpha-2b (Schering, USA) or 27 ng/g body weight Dexamethasone (Fujisawa, Deerfield, Ill.) were administered to mice intramuscularly daily for 15 consecutive days.

Dexamethasone significantly upregulated viral replication. After withdrawal of dexamethasone, the level of WHV replication remained at higher levels compared with pretreatment levels. In contrast, treatment with interferon-alpha downregulated WHV replication in mouse #1063 by greater than four logs to non-detectable levels in serum dot blots after 15 days. However, upon withdrawal of interferon-alpha, WHV replication rebounded to levels higher than pretreatment WHV levels. Mouse #1418, with higher WHV pretreatment levels than mouse #1063, showed only a limited response to interferon-alpha treatment, although with a rebound effect upon viral replication similar to mouse #1063 after drug withdrawal.

The data show a transient reduction in WHV DNA in sera after 15 days of interferon-alpha treatment as well as enhanced WHV replication by stimulation of the Glucocorticold Responsive Element with dexamethasone. The immediate rebound of viral replication after withdrawal of interferon-alpha strongly suggests that WHV DNA was not cleared from woodchuck hepatocytes and that woodchuck hepatocytes were not eliminated as a result of interferon-alpha treatment. The effectiveness of human interferon-alpha against WHV suggests that other human and murine reagents will cross react with their woodchuck homologues. The discussion of the possible mechanisms involved herein are not to be construed as limiting.

EXAMPLE 13

Figure 5A:
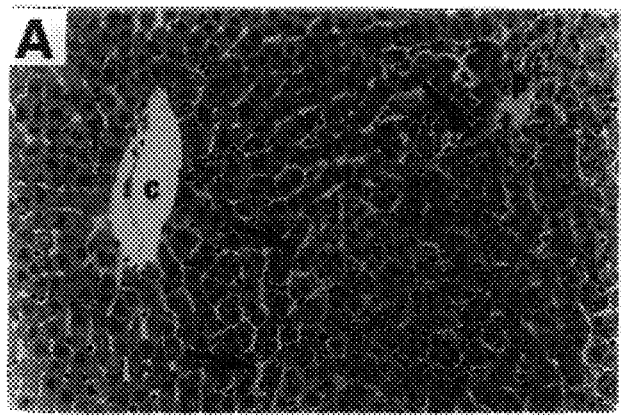
FIGS. 5(A)–(H) is a series of photographs which depict H&E staining of liver sections.
Figure 5B:
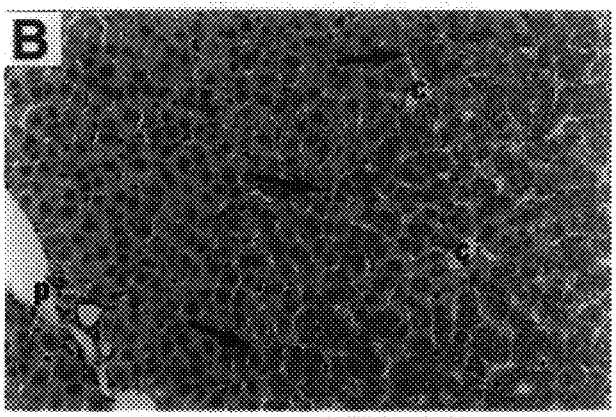
Figure 5C:
Figure 5D:
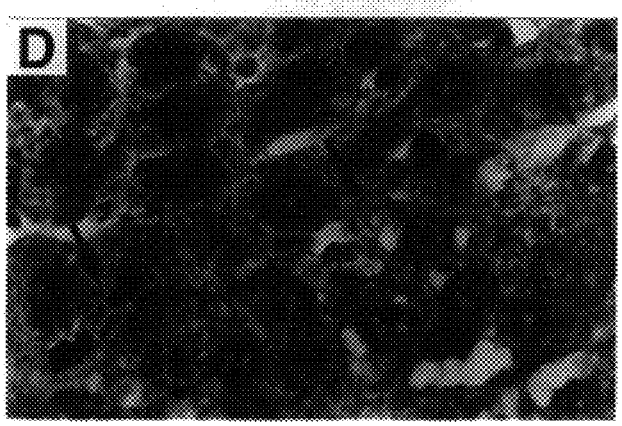

Heterogeneous Precancerous and Malignant Phenotypes of Transplanted Woodchuck Hepatocytes in Chimeric uPA/RAG-2 Mice The phenotypes of transplanted woodchuck hepatocytes in relation to hepatocytes present in the donor woodchuck were compared. In the chronic carrier woodchuck #2765, precancerous altered hepatic foci (AHF) were rare and comprised at the most, 1% of the total number of hepatocytes, according to H&E staining of liver sections (FIG. 5A, 200×). In contrast, nearly all of the nodules in the corresponding chimeric uPA/RAG-2 mouse livers had a distinct AHF phenotype (FIG. 5B, 200×) which was absent in control nontransplanted mouse livers. The hepatocytes present in the AHFs of chimeric uPA/RAG-2 mice (FIG. 5D, 1000×) were clearly different from normal woodchuck (FIG. 5C, 1000×) or normal mouse hepatocytes in that they contained large nuclei with very prominent nucleoli.

Figure 5E:
Figure 5F:
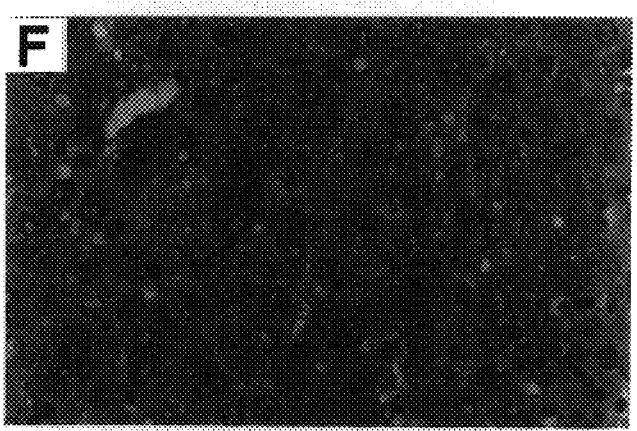
Figure 5G:
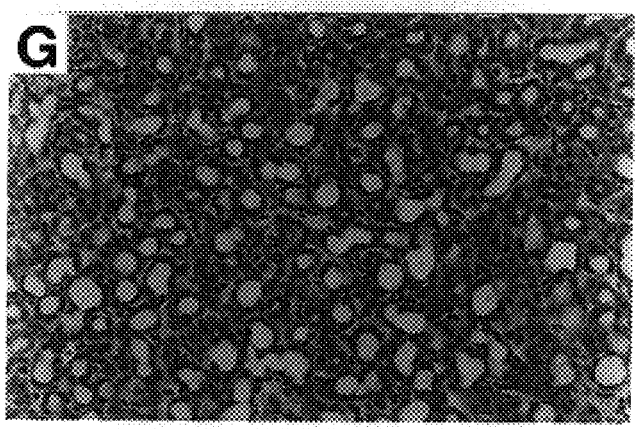
Figure 5H:
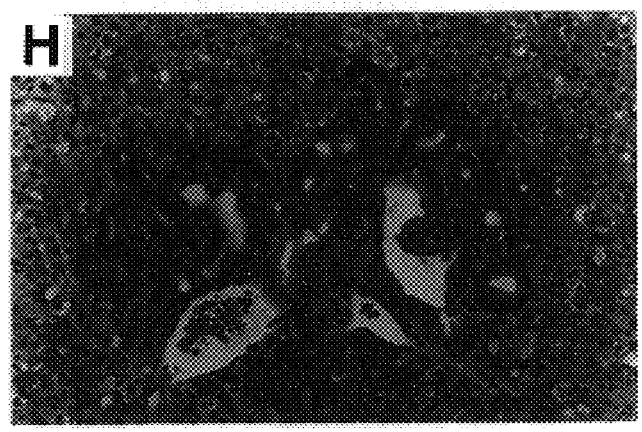

Also detected were a primary hepatocellular carcinoma (HCC) (FIG. 5F, 200×) and a cholangiocarcinorna (FIG. 5H, 200×) derived from WHV-infected woodchuck cells after transplantation into a uPA/RAG-2 mouse liver. The donor cells came from a chronic WHV carrier woodchuck (#4940) which had developed three HCCs and a cholangiocarcinoma (FIGS. 5E and 5G, respectively, each at 200×). HCC and cholanglocarcinorna, respectively, came from a woodchuck (#4940) chronically infected with WHV (200× each).

Figure 6A:
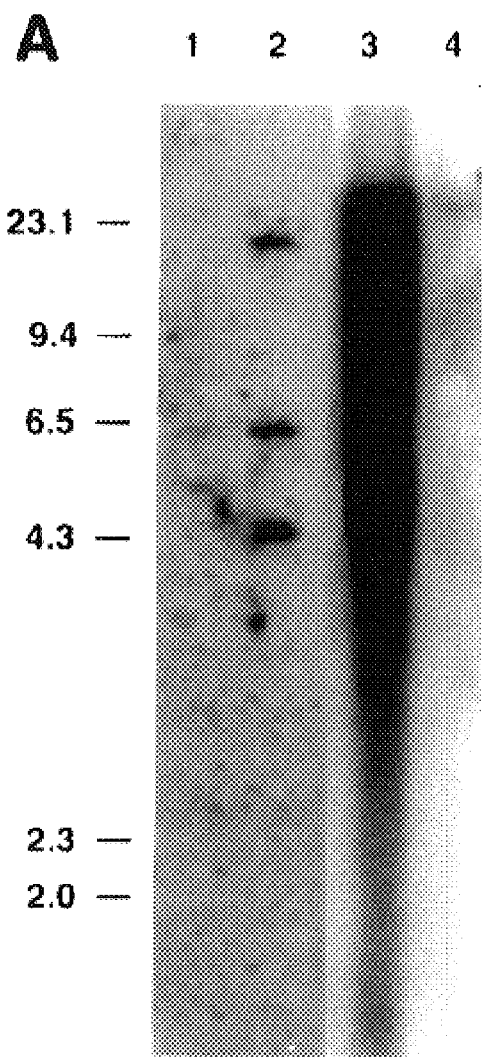
FIGS. 6(A) and (B) are photographs of Southern blots.
Figure 6B:
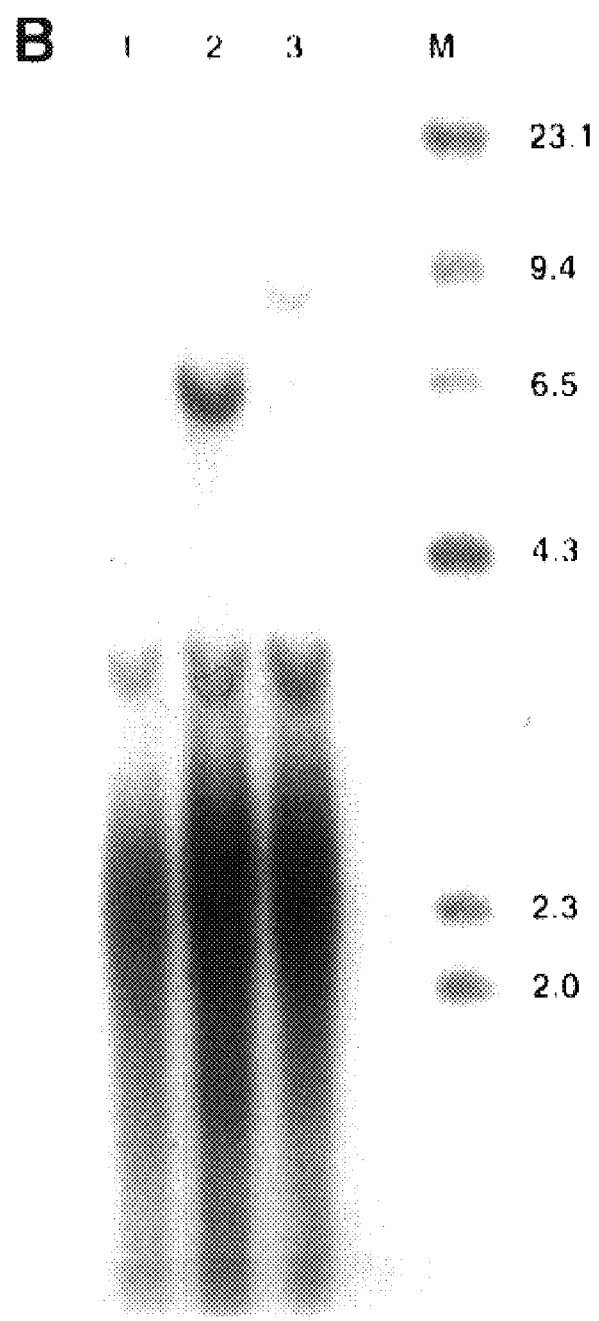
FIG. 6(B) depicts Southern blot analysis of tumor DNAs from HCCs present in the original donor woodchuck liver used to make the chimeric liver analyzed in 6A.

FIG. 6A provides Southern blot analysis of HCC tumor DNA from a chimeric uPA/RAG-2 mouse liver, hybridized with woodchuck genomic DNA (6A lanes 3 and 4) or WHV DNA probe, (6A, lanes 1 and 2). The Figure shows that woodchuck DNA was detectable in the tumor arising in the uPA/RAG-2 chimeric mouse (lane 3, with lane 4 as a negative control). In addition, unique WHV DNA integrations were identified in the DNA from the same tumor tested in lane 3 using a WHV DNA probe (lane 2, with lane 1 as negative control). FIG. 6B demonstrates that the WHV DNA integrations present in the chimeric mouse livers were different from the WHV DNA integrations in the original donor woodchuck tumor DNA samples because the WHV DNA integrations in the donor woodchuck tumor were different sizes then those present in the chimeric uPA/RAG2 mouse liver tumor (compare 6B lanes 1–3 versus 6A lane 2). These data clearly demonstrated that a new HCC developed in the chimeric mouse liver showing that liver tumor genesis occurs in lab transplanted livers. In this model, a transplanted woodchuck hepatocyte may have obtained a tumorigenic mutation during growth in the chimeric liver leading to malignant transformation. The discussion of the possible mechanisms involved herein are not to be construed as limiting.

EXAMPLE 14

Repopulation of UPA/RAG-2 Mouse Livers with Human Hepatocytes Followed by In Vivo Infection with HBV.

Human donor livers or liver segments that were denied for human liver transplantation were used to obtain primary humanhepatocytes to be used in the liver cell transplantation procedures as outlined in Example 1. Briefly, primary human hepatocytes were isolated according to the two-step collagenase perfusion method followed by differential and percoll gradient centrifugation (24). Hepatocyte viability was >80% as measured by trypan blue dye exclusion. $1 \times 10^6$ human hepatocytes were transplanted into a number of 10–14 day old UPA/RAG-2 mice by intrasplenic injection. Transplanted human hepatocytes were detectable in the perisinusoidal area 24 hours after transplantation. Normal adult human hepatocytes proliferated and were found to integrate into the recipient mouse liver cord structure, where, at 6 weeks after transplantation, they had reconstituted approximately 10% of the UPA/RAG-2 mouse livers. Human serum albumin was detected in mouse sera by PAGE/Western blot analysis.

The UPA/RAG-2 chimeric mice containing human hepatocytes were infected with human HBV as shown by the presence of hepatitis B surface antigen in the chimeric mouse serum by ELISA and immunoblotting. HBV coreprotein was detected histochemically in serial cryostat sections of UPA/RAG-2 mouse livers. Quantitative PCR demonstrated viral titers up to $1 \times 10^9$ virions/mL 6 weeks after transplantation. No inflammatory host immune response was observed in the chimeraic livers of the HBV-replicating mice.

The foregoing examples demonstrate experiments performed and contemplated by the present inventor in making and carrying out the invention. It is believed that these examples disclose various techniques which serve to demonstrate the practice of and usefulness of the invention. It will be appreciated by those skilled in the art that various changes may be made in the embodiments and techniques exemplified without departing from the scope of the invention.

REFERENCES

1. Ganem, D., and Varmus, H. E. (1987) *Annu. Rev. Biochem.* 56:651–693.
2. Buendia, M. A. (1992) *Adv. Cancer Res.* 59:167–226.
3. B. S. Blumberg. (1997) *Proc. Nad. Acad. Sci. USA* 94:7121–7125.
4. Rogler, C. E. (1991) *Curr. Top. Microbiol. Immunol.* 168:103–141.
5. Fried, M. W. (1996) *Medical Clinics of North America* 80:957–971.
6. Perillo, R. P., & Mason, A. L. (1994) *Gastroenterology Clinics of North America* 23:581–601.
7. Perillo, R. P., Schiff, E. R., Davis, G. L., Bodenheimer, H. C., Lindsay, K et al. (1990) *NEJM* 323:295–301.
8. Haria, M., & Benfield, P. (1995). *Drugs* 50:873–896.
9. Yamashita, Y., Koike, K., Takashi, M., & Matsuda, S. (1988) *Microbiol Immunol* 32: 1119–1126.
10. Nagahata,.T., Araki, K., Yamamura, K. I., & Matsubara, K. (1992) *Antimicrobial Agents Chemother* 36:2042–2045.
11. Chisari, F. V., & Ferrari, C. (1995) *Annu. Rev. Immunol.* 13:29–60.
12. Chisari, F. V. (1996) *Curr Topics Microbiol Immunol* 206:150–173.
13. Guidotti, L. G., Ando, K., Hobbs, M. V., Ishikawa, T., Runkel, L., Schreiber, R. D. & Chisari, F. V. (1994) *Proc. Natl. Acad. Sci. USA* 91:3764–3768.
14. Guidotti, L. G., Ishikawa, T., Hobbs, M. V., Matzke, B., Schreiber, R., & Chisari, F. V. (1996) *Immunity* 4:25–36.
15. Gupta, S., Rajvanshi, P., Bhargava, K. K., & Kerr, A. (1996) *Prog Liv Dis* 14:199–222.
16. Slandgren, E. P., Palmiter, R. D., Heckel, J. L., Daugherty, C. C., Brinster, R. L., & Degen, J. L. (1991) *Cell* 66:245–256.
17. Rhim, J. A., Sandgren, E. P., Degen, J. L., Palmiter, R. D., & Brinster, R. L. (1994) *Science* 263:1149–1152.
18. Rhim, J. A., Sandgren, E. P., Palmiter, R. D., and Brinster, R. L. (1995) *Proc. Natl. Acad. Sci. USA* 92:4942–4946.
19. Roggendorf, M., & Tolle, T. K. (1995) *Intervirology* 38:100–112.
20. Karba, B. E., Cote, P. J., Wells, F. N., Baldwin, B., Popper, H., Purcell, R. H., Tennant, B. C., & Gerin, J. L. (1989). *J Virol* 63:1360–70.
21. Tennant, B. C., & Gerin, J. L. (1994) in *The Liver. Biologyand Pathobiology*, eds. Arias, I. M., Boyer, J. L., Fausto, N., Jakoby, W. B., Schachter, D., & Shafritz, D. A. (Raven Press,. New York) pp 1455–1469.
22. Shinkai, Y., Rathbun, G., Lam, K. P., Oltz, E. M., Stewart, V., Mendelsohn, M., Charron, J., Datta, M., Young, F., Stall, A. M., & Alt, F. W. (1992) *Cell* 68:855–867.
23. Horton, R. M., Karachunski, P. I., & Conti-Fine, B. M. (1995) *Bio Techniques* 19:690–691.
24. Gupta S., Vemuru. R. P., Lee, C. D., Yemeni, P., Aragona, E., & Burk, R. D. (1994) *Human Gene Ther* 4:249–257.
25. Vemuru, R. P., Aragona, E., & Gupta, S. (1992) *Hepatology* 16:968–73.
26. Laemmli, U. K. (1970). *Nature* 227:680–685.
27. Gong, S. S., Jensen, A. D., & Rogler, C. E. (1996). *J. Virol.* 70:2000–2007.
28.: Petersen, J., Buerkle, A., Zhang, L., & Rogler, C. E. (1997) *J. Virol.* 71:5455–5463.
29. Ogston, C. W., Jonak, G. J., Rogler, C. E., Astrin, S. M., & Summers, J. (1982) *Cell* 29:385–394.
30. Dandri, M., Schirmacher, P., & Rogler, C. E. (1996). *J. Virol.* 70:5246–5254.
31. Rajvanshi, P., Kerr, A., Bhargava, K. K., Burk, R. D., & Gupta, S. (1996) *Hepatology* 23:482–496.
32. Scotto, J., Hadchouel, M., Hery, C., Yvart, Y., Tiollais, P., & Brechot, C. (1983) *Hepatology* 3:279–284.

What is claimed is:

1. A method of making a chimeric mouse, comprising:
   a) creating an immunetolerant mouse lacking functional T and B cells and having a genome which comprises a urokinase-type plasminogen activator (uPA) gene, expression of said uPA gene resulting in liver degeneration;
   b) repopulating the parenchyma of the degenerated liver by transplanting xenogenic mammalian hepatocytes that are a natural host for infection with one or more compatible hepatitis virus into said liver; and
   c) infecting the xenogenic mammalian hepatocytes with said one or more compatible hepatitis virus, said one or more compatible hepatitis virus selected from the group consisting of mammalian hepatitis A virus, hepatitis D virus coinfected with hepadnavirus, hepatitis E virus, hepatitis F virus and hepadnavirus,
   thereby making said chimeric mouse.

2. The method of claim 1, which comprises infecting the xenogenic mammalian hepatocytes with hepatitis virus prior to said transplanting.

3. The method of claim 1, which comprises infecting the xenogenic mammalian hepatocytes with hepatitis virus following said repopulation.

4. The method of claim 1, wherein the xenogenic mammalian hepatocytes are selected from the group consisting of human, chimpanzee, baboon, wooly monkey, ground squirrel, and woodchuck hepatocytes.

5. The method of claim 4, wherein the xenogenic mammalian hepatocytes are human hepatocytes and the compatible mammalian hepatitis virus is human hepatitis B virus.

6. The method of claim 1, wherein the immunetolerant mouse which has a degenerated liver is created by:
   a) crossing a hemizygous or homozygous urokinase-type plasminogen activator (uPA) transgenic mouse with a homozygous Recombination Activation Gene 2 (RAG-2) knockout mouse to generate F1 uPA hemizygous, RAG-2 hemizygous sibling mice; and
   b) crossing the F1 mouse to another sibling F1 mouse or to a RAG2 homozygous mouse to generate a uPA hemizygous or homozygous, RAG2 homozygous (uPA/RAG2) F2 mouse.

7. The method of claim 6, wherein the xenogenic mammalian hepatocytes are from a woodchuck and the compatible mammalian hepatitis virus is Woodchuck Hepatitis Virus (WHV).

8. A chimeric mouse model system for hepatitis comprising:
   an immunetolerant mouse lacking functional T and B cells,
   said immunetolerant mouse having a degenerated liver parenchyma due to expression of a urokinase-type plasminogen activator (uPA) gene present in the genome of said immunetolerant mouse, and said degenerated liver being repopulated with transplanted xenogenic mammalian hepatocytes that are infected with at least one compatible mammalian hepatitis virus, and
   said at least one compatible mammalian hepatitis virus is selected from the group consisting of hepatitis A virus, hepatitis D virus coinfected with hepadnavirus, hepatitis E virus, hepatitis F virus and hepadnavirus.

9. The chimeric mouse model system of claim 8, wherein the xenogenic mammalian hepatocytes are infected with hepatitis virus prior to said transplantation.

10. The chimeric mouse model system of claim 8, wherein the xenogenic mammalian hepatocytes are infected with hepatitis virus following said repopulation.

11. The chimeric mouse model system of claim 8, wherein the xenogenic mammalian hepatocytes are selected from the group consisting of human, chimpanzee, baboon, wooly monkey, ground squirrel, and woodchuck hepatocytes.

12. The chimeric mouse model system of claim 11, wherein the xenogenic mammalian hepatocytes are human hepatocytes and the compatible mammalian hepatitis virus is hepatitis B virus.

13. The chimeric mouse model system of claim 8, wherein the immunetolerant mouse having degenerated liver parenchyma is hemizygous or homozygous for said urokinase-type plasminogen activator (uPA) gene and is homozygous for a Recombination Activation Gene 2 (RAG-2) knockout mutation.

14. The chimeric mouse model system of claim 13, wherein the source of the xenogenic mammalian hepatocytes is a woodchuck and the compatible mammalian hepatitis virus is Woodchuck Hepatitis Virus (WHV).

15. A method for screening a test compound for anti-viral activity, comprising:
   a) administering said test compound to an immunetolerant chimeric mouse lacking functional T and B cells which has a degenerated liver parenchyma due to expression of a urokinase-type plasminogen activator (uPA) gene present in the genome of said immunetolerant chimeric mouse, said degenerated liver being repopulated with transplanted xenogenic mammalian hepatocytes that are infected with at least one compatible mammalian hepatitis virus selected from the group consisting of hepatitis A virus, hepatitis D virus coinfected with hepadnavirus, hepatitis E virus, hepatitis F virus and hepadnavirus; and
   b) assaying the level of replication of the virus;
thereby screening said test compound for anti-viral activity.

16. The method of claim 15, wherein the mammalian hepatitis virus is hepatitis B virus.

17. The method of claim 15, which comprises comparing the level of viral replication in said mouse and in a control mouse which has not been administered the test compound.

18. The method of claim 15, wherein the xenogenic mammalian hepatocytes were infected with the compatible mammalian hepatitis virus prior to said transplanting.

19. The method of claim 16, wherein the xenogenic mammalian hepatocytes were infected with the compatible mammalian hepatitis virus following said repopulating step.

20. The method of claim 15, which comprises selecting the xenogenic mammalian hepatocytes from the group consisting of human, chimpanzee, baboon, wooly monkey, ground squirrel, and woodchuck hepatocytes.

21. The method of claim 20, wherein the xenogenic mammalian hepatocytes are human hepatocytes and the compatible mammalian virus is hepatitis B virus.

22. The method of claim 15, wherein the immunetolerant mouse which has a degenerated liver is hemizygous or homozygous for said urokinase-type plasminogen activator (uPA) gene and homozygous for a Recombination Activation Gene 2 (RAG-2) knockout mutation.

23. The method of claim 22, wherein the source of the xenogenic mammalian hepatocytes is a woodchuck and the compatible mammalian hepatitis virus is Woodchuck Hepatitis Virus (WHV).

24. The method of claim 15, wherein the antiviral compound is a member selected from the group consisting of interferons, cytokines, interleukins, growth factors, hormones, nucleoside analogues, and antisense DNA/RNA.

25. A method for screening a test compound for anti-cancer activity, comprising:
   a) administering said test compound to immunetolerant chimeric mice lacking functional T and B cells,
   said mice having a degenerated liver parenchyma due to expression of a urokinase-type plasminogen activator (uPA) gene present in the genome of said immunetolerant chimeric mice,
   said degenerated liver parenchyma being repopulated with transplanted xenogenic mammalian hepatocytes that are infected with at least one compatible mammalian hepatitis virus capable of causing hepatocellular carcinoma in said xenogenic hepatocytes,
   where said at least one compatible mammalian hepatitis virus is selected from the group consisting of hepatitis A virus, hepatitis D virus coinfected with hepadnavirus, hepatitis E virus, hepatitis F virus and hepadnavirus;
   b) assaying said mice for the development of hepatocellular carcinoma virus; and
   c) comparing the assay in the chimeric mice with the same assay carried out in control mice which have not been administered the test compound,
   wherein the chimeric mice have precancerous or malignant cancerous hepatic tissue and wherein the development of hepatocellular carcinomas is assayed by monitoring for the prevention of the development of cancerous tissue from precancerous tissue or the amelioration of the malignant cancerous tissue,
   thereby screening said test compound for anti-cancer activity.

26. The method of claim 25, which comprises comparing the presence of unique viral DNA integrations in the livers of said mice and in control mice which have not been administered the test compound.

27. The method of claim 25, wherein the xenogenic mammalian hepatocytes were infected with a hepatitis virus prior to said transplantation step.

28. The method of claim 25, wherein the xenogenic mammalian hepatocytes were infected with hepatitis virus following said repopulating step.

29. The method of claim 25, wherein the xenogenic mammalian hepatocytes are selected from the group consisting of human, chimpanzee, baboon, wooly monkey, ground squirrels and woodchuck hepatocytes.

30. The method of claim 29, wherein the xenogenic mammalian hepatocytes are human hepatocytes and the compatible mammalian hepatitis virus is hepatitis B virus.

31. The method of claim 25, wherein the immunetolerant mice which have a degenerated liver are hemizygous or homozygous for said urokinase-type plasminogen activator (uPA) gene and homozygous for a Recombination Activation Gene 2 (RAG-2) knockout mutation.

32. The method of claim 30, wherein the source of the xenogenic mammalian hepatocytes is a woodchuck and the compatible mammalian hepatitis virus is Woodchuck Hepatitis Virus (WHV).

33. The method of claim 25, wherein the anticancer compound is a member selected from the group consisting of interferons, cytokines, interleukins, growth factors, hormones, nucleoside analogues, and antisense DNA/RNA.

34. A method of making a chimeric mouse, comprising:
   a) creating an immunetolerant mouse, said immunetolerant mouse having a degenerated liver due to expression of a urokinase-type plasminogen activator (uPA) gene and lacking functional T and B cells, said uPA gene being present in the genome of said immunetolerant mouse;
   b) transplanting human hepatocytes having at least 80% viability by intrasplenic injection to repopulate the parenchyma of the degenerated liver; and
   c) infecting said hepatocytes with one or more compatible hepatitis virus selected from the group consisting of hepatitis A virus, hepatitis D virus coinfected with hepadnavirus, hepatitis E virus, hepatitis F virus and hepadnavirus,
   thereby making said chimeric mouse.

35. The method of claim 34, wherein said immunetolerant mouse is about 10–14 days old at the time of transplanting said human hepatocytes.

36. The method of claim 35, wherein the transplanted human hepatocytes reconstitute approximately 10% of the degenerated liver.

37. The method of claim 1, wherein said uPA gene encodes secreted uPA.

38. The chimeric mouse model system of claim 8, wherein said uPA gene encodes secreted uPA.

39. The method of claim 15, wherein said uPA gene encodes secreted uPA.

40. The method of claim 25, wherein said uPA gene encodes secreted uPA.

41. The method of claim 34, wherein said uPA gene encodes secreted uPA.

42. The method of claim 34, which comprises infecting said hepatocytes with hepatitis virus prior to said transplanting.

43. The method of claim 34, which comprises infecting said hepatocytes with hepatitis virus following said repopulation.

44. The method of claim 34, which comprises infecting said hepatocytes with hepatitis B virus.

45. A method of making a chimeric mouse, comprising:

a) creating an immunetolerant mouse lacking functional T and B cells and having a genome which comprises a urokinase-type plasminogen activator (uPA) gene, expression of said uPA gene resulting in liver degeneration;

b) repopulating the parenchyma of the degenerated liver by transplanting human hepatocytes into said liver; and c) infecting said human hepatocytes with human hepatitis B virus, thereby making said chimeric mouse.

46. A chimeric mouse model system for hepatitis comprising:

an immunetolerant mouse lacking functional T and B cells, said immunetolerant mouse having a degenerated liver parenchyma due to expression of a urokinase-type plasminogen activator (uPA) gene present in the genome of said immunetolerant mouse, and said degenerated liver being repopulated with transplanted human hepatocytes that are infected with human hepatitis B virus.

* * * * *

UNITED STATES PATENT AND TRADEMARK OFFICE
CERTIFICATE OF CORRECTION

PATENT NO.    : 6,864,402 B1
DATED         : March 8, 2005
INVENTOR(S)   : Joerg Petersen et al.

It is certified that error appears in the above-identified patent and that said Letters Patent is hereby corrected as shown below:

Title page,
Item [75], Inventors, please delete "Charles E. Rogler, Lawthorne, NY" and substitute with -- Charles E. Rogler, Carmel, NY --.

Signed and Sealed this

Twenty-fourth Day of May, 2005

JON W. DUDAS
*Director of the United States Patent and Trademark Office*

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide primers

<400> SEQUENCE: 1
catccctgtg acccctcc                                                    18

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 2
ctccaaacca cccccctc                                                    18